United States Patent
Pelizzari et al.

(10) Patent No.: US 7,265,356 B2
(45) Date of Patent: Sep. 4, 2007

(54) IMAGE-GUIDED MEDICAL INTERVENTION APPARATUS AND METHOD

(75) Inventors: Charles A. Pelizzari, Chicago, IL (US); Chin-Tu Chen, Lisle, IL (US); Ralph R. Weichselbaum, Chicago, IL (US); Samuel Hellman, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 10/998,509

(22) Filed: Nov. 29, 2004

(65) Prior Publication Data

US 2006/0113482 A1 Jun. 1, 2006

(51) Int. Cl.
G01T 1/24 (2006.01)
(52) U.S. Cl. .................................. 250/370.09
(58) Field of Classification Search ............ 250/370.09
See application file for complete search history.

(56) References Cited

U.S. PATENT DOCUMENTS

| | | | |
|---|---|---|---|
| 4,939,464 A | 7/1990 | Hammer | |
| 5,289,008 A | 2/1994 | Jaszczak et al. | |
| 5,672,877 A | 9/1997 | Liebig et al. | |
| 6,114,701 A | 9/2000 | Plummer et al. | |
| 6,205,347 B1 | 3/2001 | Morgan et al. | |
| 6,339,223 B1 | 1/2002 | Motomura et al. | |
| 6,388,244 B1 | 5/2002 | Gagnon | |
| 6,399,951 B1 * | 6/2002 | Paulus et al. | 250/370.13 |
| 6,448,559 B1 * | 9/2002 | Saoudi et al. | 250/367 |
| 6,449,331 B1 | 9/2002 | Nutt et al. | |
| 6,490,476 B1 | 12/2002 | Townsend et al. | |
| 6,631,284 B2 | 10/2003 | Nutt et al. | |
| 6,661,870 B2 | 12/2003 | Kapatoes et al. | |
| 6,700,949 B2 | 3/2004 | Susami et al. | |
| 6,754,519 B1 | 6/2004 | Hefetz et al. | |
| 6,754,520 B2 | 6/2004 | DeSilets et al. | |
| 6,888,919 B2 * | 5/2005 | Graf | 378/65 |
| 6,963,065 B2 | 11/2005 | Conti et al. | |

(Continued)

OTHER PUBLICATIONS

Elekta, Image-Guided Radiotherapy (IGRT), 3 pages, publicly available prior to filing date of application.

(Continued)

Primary Examiner—David Porta
Assistant Examiner—Marcus Taningco
(74) Attorney, Agent, or Firm—Michael Best & Friedrich

(57) ABSTRACT

In some embodiments, an image-guided radiotherapy apparatus and method is provided in which a radiotherapy radiation source and a gamma ray photon imaging device are positioned with respect to a patient area so that a patient can be treated by a beam emitted from the radiotherapy apparatus and can have images taken by the gamma ray photon imaging device. Radiotherapy treatment and imaging can be performed substantially simultaneously and/or can be performed without moving the patient in some embodiments. The gamma ray photon imaging device can be coupled and movable with respect to any part of a building structure, can be located on a portable frame movable to and from the radiotherapy radiation source and patient, or can take other forms. In some embodiments, the gamma ray photon imaging device can be used for imaging in connection with other types of medical interventions.

59 Claims, 8 Drawing Sheets

U.S. PATENT DOCUMENTS

| | | |
|---|---|---|
| 7,020,233 B1 * | 3/2006 | Tybinkowski et al. ......... 378/4 |
| 2002/0090050 A1 | 7/2002 | Nutt et al. |
| 2003/0004405 A1 | 1/2003 | Townsend et al. |
| 2003/0128801 A1 * | 7/2003 | Eisenberg et al. ............ 378/19 |
| 2004/0030246 A1 | 2/2004 | Townsend et al. |
| 2004/0167398 A1 | 8/2004 | Flohr et al. |
| 2004/0206897 A1 | 10/2004 | Conti et al. |
| 2005/0067578 A1 * | 3/2005 | Ueno et al. ............ 250/370.09 |

OTHER PUBLICATIONS

Siemens Medical, IGRT: Image-Guided Radiation Therapy, a Picture of Greater Certainty, 7 pages, publicly available prior to filing date of application.

Varian Medical Systems, 2 website printout pages dated Sep. 29, 2004.

* cited by examiner

IMAGE-GUIDED MEDICAL INTERVENTION APPARATUS AND METHOD

BACKGROUND OF THE INVENTION

In virtually all fields of medicine, the pace of technological developments continues to drive the need for improved medical imaging devices and methods. Such devices and methods are commonly employed in conjunction with many different types of medical interventions, such as radiotherapy, surgery, biopsies, and the like.

In many cases, however, conventional medical imaging systems and methods are either unsuitable for many types of medical interventions or are limited in application in one or more significant manners. By way of example only, the effectiveness of conventional radiotherapy systems and methods is typically a function of medical image accuracy. After medical images of a patient have been taken in order to determine the location of one or more body areas requiring radiation therapy, some degree of error is generated by patient movement (whether voluntary or involuntary). As a result, the precise locations of the body areas are often slightly different than those indicated by the medical images. This discrepancy can reduce the effectiveness of the radiation therapy, and in some cases can require that such therapy be prolonged and/or reduced in dose.

As another example, many types of medical interventions cannot be performed in conjunction with conventional medical imaging systems without moving the patient or moving the medical intervention apparatus to gain access to the patient. Such movement can require interruption of medical imaging, compromise the quality of the medical images, reduce the effectiveness of the medical intervention, or have other undesirable effects. For example, many types of computed tomography (CT) imaging, magnetic resonance imaging (MRI), and Positron Emission Tomography (PET) imaging devices at least partially enclose a patient, or otherwise significantly limit free access to the patient for medical intervention procedures. Therefore, medical intervention procedures are commonly performed after the patient or equipment is moved to gain or increase access to the patient. Such movement typically results in one or more of the undesirable results mentioned above.

As the demand for improved medical intervention procedures continues to grow, the demand for new medical imaging devices and methods needed to perform such procedures also grows. New devices and methods for image-guided medical intervention are therefore welcome additions to the art.

SUMMARY OF THE INVENTION

Some embodiments of the present invention provide an image-guided radiotherapy apparatus, comprising a gantry movable about a patient area; a radiation source from which radiation is emitted toward the patient area, the radiation source coupled to and movable with the gantry to different positions about the patient area; and a gamma ray photon imaging device comprising a gamma ray photon detector proximate the patient area and positioned to receive and detect gamma ray photons emitted from within the patient area, the gamma ray photon detector movable to different positions about the patient area to obtain different images of a patient within the patient area.

In some embodiments, an image-guided radiotherapy apparatus for treatment of a patient is provided, and comprises a gantry; a radiotherapy accelerator adapted to generate a beam of at least one of X-rays, gamma rays, and electrons, the radiotherapy accelerator coupled to the gantry and movable through a range of different positions and orientations to change trajectory of the beam; and a PET detector coupled to the gantry and movable through a range of different positions and orientations about a patient area in which a patient's PET image can be taken, the patient area comprising at least one location through which the beam of the radiotherapy accelerator passes in at least one position and orientation of the radiotherapy accelerator.

Some embodiments of the present invention provide a method of administering image-guided radiotherapy, comprising adjusting at least one of a position and orientation of a radiotherapy radiation source with respect to a patient; changing a radiation trajectory of the radiotherapy radiation source to a desired radiation trajectory by adjusting the at least one of a position and orientation of the radiotherapy radiation source, the desired radiation trajectory passing through the patient; adjusting at least one of a position and orientation of a gamma ray photon imaging device with respect to the patient; detecting gamma ray photons with the gamma ray photon imaging device, the gamma ray photons emitted from the patient proximate a location along the desired radiation trajectory at which the desired radiation trajectory intersects the patient; and generating an image representative of the patient based at least in part upon locations on the gamma ray photon imaging device at which gamma ray photons are detected.

Further aspects of the present invention, together with the organization and operation thereof, will become apparent from the following detailed description of the invention when taken in conjunction with the accompanying drawings, wherein like elements have like numerals throughout the drawings.

Figure 1:
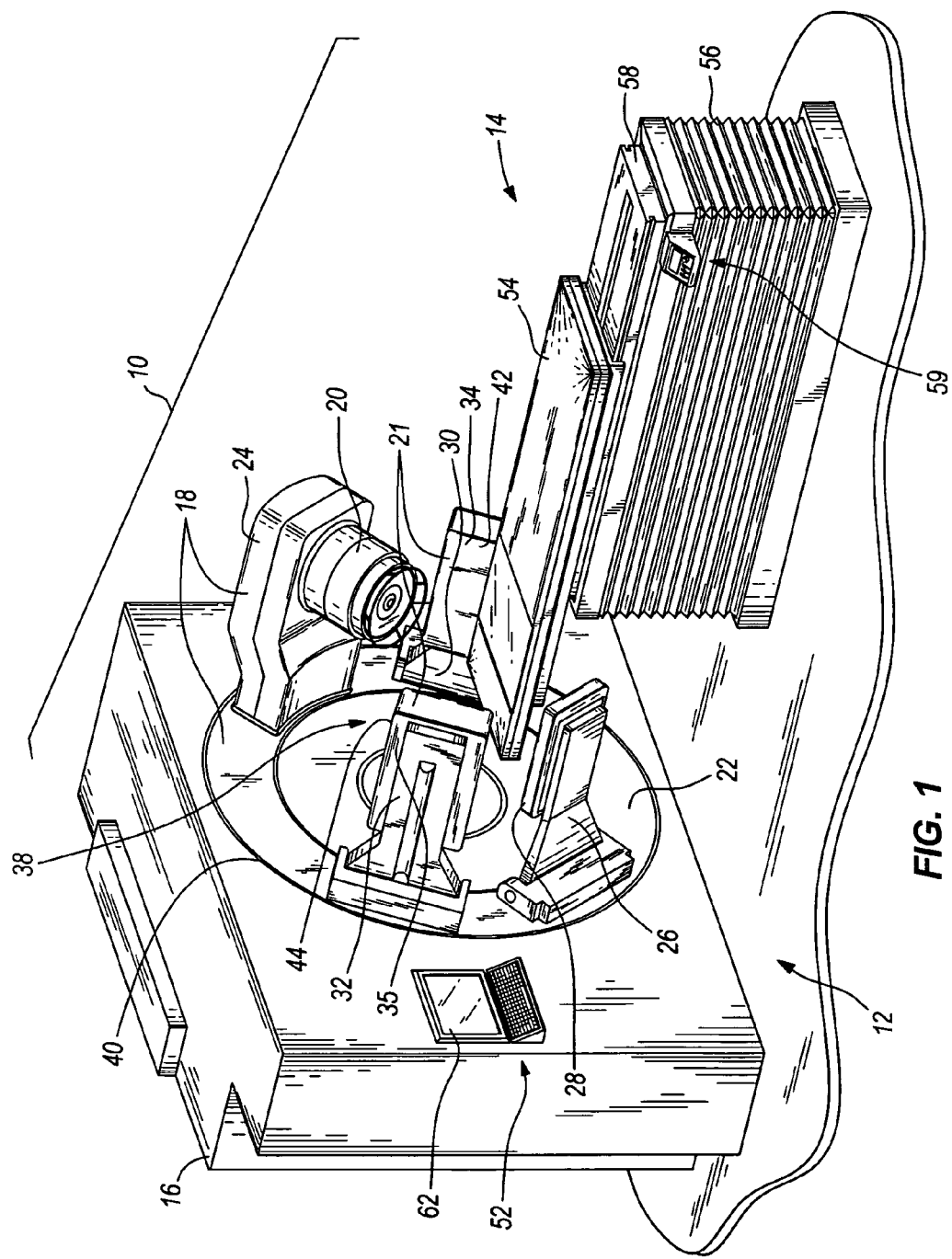
FIG. 1 is a perspective view of an image-guided radiotherapy apparatus according to a first embodiment of the present invention.

Before the various embodiments of the present invention are explained in detail, it is to be understood that the invention is not limited in its application to the details of construction and the arrangements of components set forth in the following description or illustrated in the drawings. The invention is capable of other embodiments and of being practiced or of being carried out in various ways. Also, it is to be understood that phraseology and terminology used herein with reference to device or element orientation (such as, for example, terms like "front", "back", "up", "down", "top", "bottom", and the like) are only used to simplify description of the present invention, and do not alone indicate or imply that the device or element referred to must have a particular orientation. In addition, terms such as "first", "second", and "third" are used herein and in the appended claims for purposes of description and are not intended to indicate or imply relative importance or significance. The use of "including," "comprising," or "having" and variations thereof herein is meant to encompass the items listed thereafter and equivalents thereof as well as additional items. Unless limited otherwise, the terms "connected," "coupled," and variations thereof herein are used broadly and encompass direct and indirect connections and couplings. In addition, the terms "connected" and "coupled" and variations thereof are not restricted to physical or mechanical connections or couplings.

DETAILED DESCRIPTION

Figure 2:
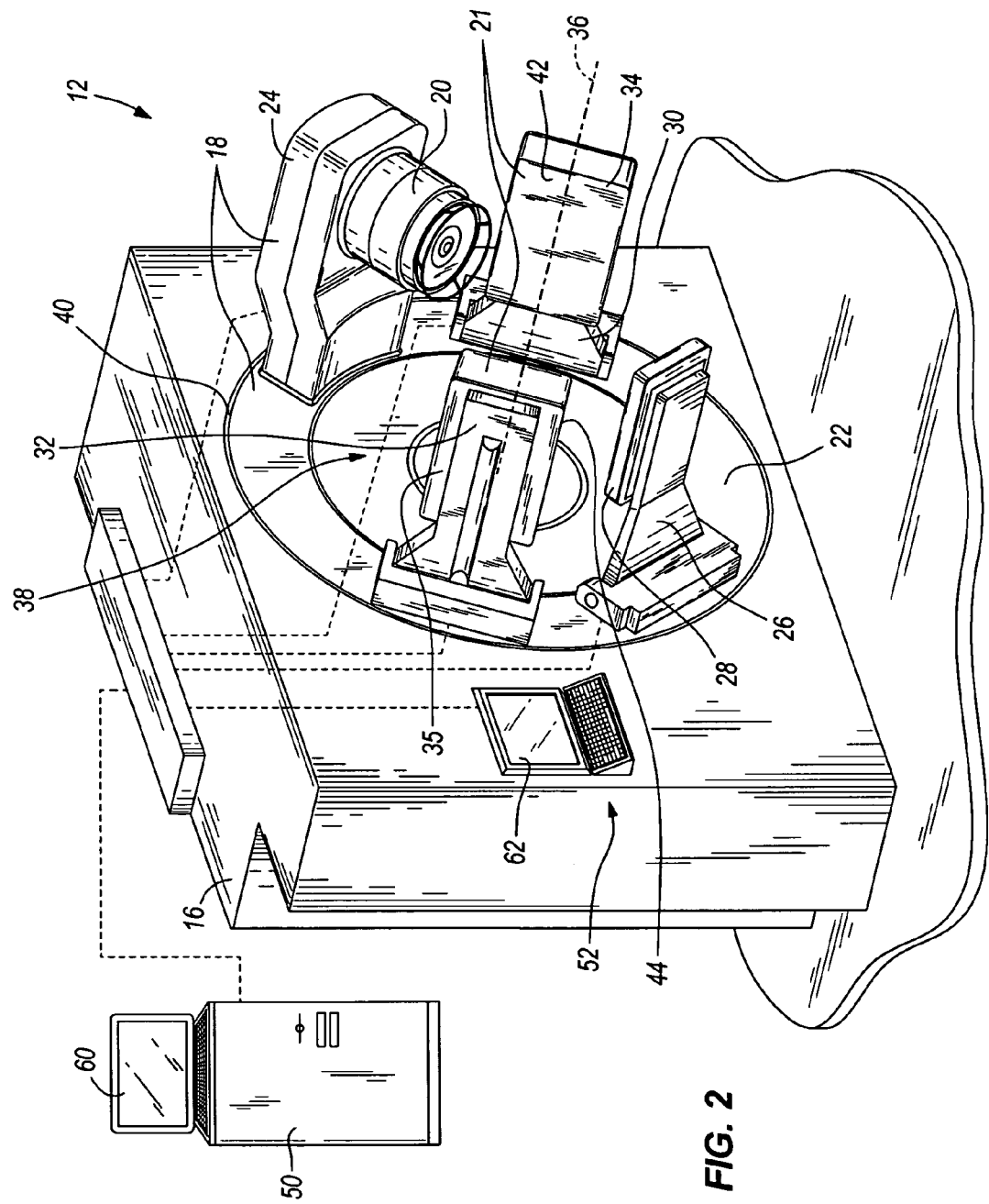
FIG. 2 is a perspective view of the radiotherapy and imaging assembly illustrated in FIG. 1.

An image-guided radiotherapy apparatus according to an embodiment of the present invention is illustrated by way of example in FIGS. 1 and 2. The illustrated apparatus (indicated generally at 10) comprises a radiotherapy and imaging assembly 12 and a patient support 14. The patient support 14 is adapted to support a patient (i.e., a human or animal) in a position with respect to the radiotherapy and imaging assembly 12 during therapy and imaging procedures as described in greater detail below.

The radiotherapy and imaging assembly 12 illustrated in FIGS. 1 and 2 comprises a housing 16, a gantry 18 movable with respect to the housing 16, a radiotherapy accelerator 20 coupled to the gantry 18, and a PET imaging device 21 coupled to the gantry 18. As will be described in greater detail below, the gantry 18 is movable to different positions for purposes of administering radiotherapy and for PET image acquisition.

The gantry 18 in the illustrated embodiment of FIGS. 1 and 2 comprises a ring 22, a first arm 24 extending from the ring 22 and to which the radiotherapy accelerator 20 is coupled, a second arm 26 extending from the ring 22 and to which a portal imager 28 is coupled, and third and fourth arms 30, 32 extending from the ring 22 and to which PET detectors 34, 35 are coupled. The ring 22 is rotatable about an axis 36 to move the arms 24, 26, 30, 32 (and therefore the radiotherapy accelerator 20, portal imager 28, and PET detectors 34, 35) about the axis 36.

The ring 22 can be driven in any conventional manner, including without limitation by a sun gear about which one or more planet gears can be driven (not shown), wherein the arms 24, 26, 30, 32 can be directly or indirectly coupled to the planet gears for movement about the axis 36, by a ring gear driven by one or more pinions or worm gears (also not shown), wherein the arms 24, 26, 30, 32 can be directly or indirectly coupled to the ring gear for movement about the axis 36, by a prime mover directly or indirectly coupled to an axle upon which a frame is mounted (also not shown), wherein the prime mover rotates the axle and frame to which the arms 24, 26, 30, 32 are coupled for movement about the axis 36. Still other manners of driving the ring 22 are possible, are known to those skilled in the art, and are not therefore described further herein.

The radiotherapy and imaging assembly 12 illustrated in FIGS. 1 and 2 has a substantially closed front facing the arms 24, 26, 30, 32 and a patient area 38 (described below) where a patient is located for radiotherapy and imaging procedures. In other embodiments, however, the radiotherapy and imaging assembly 12 has a blind aperture or an aperture extending through the housing 16, in which case the patient can be positioned at least partially within the housing 16 for radiotherapy and/or imaging procedures. The selection of a drive assembly (described above) used to drive the ring 22 can be dependent at least in part upon the existence, location, and size of such an aperture.

The ring 22 can have any shape and size suitable for supporting the arms 24, 26, 30, 32. In this regard, the arms 24, 26, 30, 32 can be supported by an annular member comprised of one or more elements, a disc having any diameter, and still other structures. As used herein, the term "ring" therefore refers to that annular structure of the radiotherapy and imaging assembly 12 to which the arms 24, 26, 30, 32 are coupled, and can be defined at least in part by one or more elements having other portions (i.e., a disc having an outer annular portion or "ring" 22).

With continued reference to the embodiment illustrated in FIGS. 1 and 2, the radiotherapy and imaging assembly 12 can have a track 40 in which the ring 22 is received and along which the ring 22 moves as the ring 22 rotates. The track 40 can have one or more bearing surfaces enabling low-friction movement between the track 40 and the ring 22. The track 40 can have any cross-sectional shape desired, including without limitation a C- or L-shaped cross-section in which the ring 22 is rotatably received, an I- or T-shaped cross-section (which can provide a web along which rollers, bearings, or other low-friction elements can move), and the like. Any track shape suitable for providing one or more surfaces along which the ring 22 can rotate and/or for retaining the ring 22 in position on the radiotherapy and imaging assembly 12 can be employed, and falls within the spirit and scope of the present invention.

Although the illustrated embodiment of FIGS. 1 and 2 utilizes a rotatable ring 22 for moving the arms 24, 26, 30, 32 as described above, it will be appreciated that the arms 24, 26, 30, 32 can be coupled to rotate about the patient area 38 in other manners. For example, one or more of the arms 24, 26, 30, 32 can be coupled to and run along the track 40 without the use of a ring 22, or can be coupled to a rotatable frame within the housing 16. Also, in those embodiments in which a rotatable ring 22 is used to rotate the arms 24, 26, 30, 32 as described above, it will be appreciated that a track 40 is not required. For example, the ring 22 can be supported by one or more bearings, pinions, bushings, and the like. Still other manners of rotating the arms 24, 26, 30, 32 about the patient area 38 are possible, and fall within the spirit and scope of the present invention.

The arms 24, 26, 30, 32 can be any length desired, and in some embodiments have a length sufficient to position the radiotherapy accelerator 20 and the PET detectors 34, 35 a distance from the housing 16. In many applications, it is desirable to maintain such a distance for patient comfort and to enable the patient to be positioned in a range of positions with respect to the radiotherapy accelerator 20 and the PET detectors 34, 35. However, in other embodiments, the radiotherapy accelerator 20 and PET detectors 34, 35 can instead be located within a blind hole or in a hole extending through the housing 16 as described above. In such embodiments, arms 24, 26, 30, 32 need not necessarily be used to position the radiotherapy accelerator 20 and PET detectors 34, 35 with respect to the patient area 38. Instead, the radiotherapy accelerator 20 and/or PET detectors 34, 35 can be mounted directly to the ring 22 (or can be mounted for movement along the track 40 as described above).

The radiotherapy accelerator 20 illustrated in FIGS. 1 and 2 is a linear accelerator producing a high-intensity X-ray beam that exits the radiotherapy accelerator 20 toward the patient area 38. In other embodiments, other devices can be used to generate other types of radiation that can be used to treat a patient. By way of example only, the arm 24 can support any device capable of emitting electrons, gamma rays, and other types of radiation toward the patient area 38. A variety of radiation-emitting devices capable of emitting a number of different types of radiation and adapted for radiotherapy exist, are well known to those in the art, and are not therefore described further herein.

By rotating the ring 22 illustrated in FIGS. 1 and 2, the arm 24 also rotates, thereby rotating the radiotherapy accelerator 20 through a range of different positions about the patient area 38. Such adjustment enables a user to change the trajectory of a beam of radiation exiting from the radiotherapy accelerator 20, thereby enabling the user to direct the beam to different desired locations in or on the patient. The ring 22 can be rotatable through any range permitting such beam control. In some embodiments, the radiotherapy accelerator 20 is rotatable to any position about the patient area 38. For example, the ring 22 can rotate through a range of 360 or more degrees in order to move the radiotherapy accelerator 20 through the same range, although smaller ranges of movement are possible.

As noted above, the radiotherapy and imaging assembly 12 can also include a portal imager 28, which can receive at least some of the radiation from the radiotherapy accelerator 20 in order to generate images of the patient. Any conventional portal imager 28 can be used for this purpose, including without limitation portal imagers 28 using radiographic film, on-line portal imagers (e.g., flat-panel and other types of electronic portal imagers), and other conventional X-ray imaging devices for acquiring anatomic images of the patient.

With continued reference to the embodiment of the present invention illustrated in FIGS. 1 and 2, the portal imager 28 can be located opposite the radiotherapy accelerator 20 across the patient area 38, and can be oriented to receive radiation emitted from the radiotherapy accelerator 20 as described above. To this end, the portal imager 28 can be located on an arm 26 (as also described above) extending from the ring 22 at a location opposite the arm 24 of the radiotherapy accelerator 20.

By rotating the ring 22 illustrated in FIGS. 1 and 2, the arm 26 supporting the portal imager 28 can also rotate, thereby rotating the portal imager 28 with the radiotherapy accelerator 20 through a range of different positions about the patient area 38. In this manner, the portal imager 28 can acquire patient images in the different positions of the radiotherapy accelerator 20. Although a portal imager 28 is provided in the embodiment illustrated in FIGS. 1 and 2, in other embodiments the radiotherapy and imaging assembly 12 has no portal imager 28.

As described above, the radiotherapy and imaging assembly 12 illustrated in FIGS. 1 and 2 also comprises a PET imaging device 21 coupled to the gantry 18. The illustrated PET imaging device 21 has first and second PET detectors 34, 35 located on respective arms 30, 32 extending from the ring 22. Each of the PET detectors 34, 35 is responsive to gamma rays released during the decay of a positron-emitting material in the patient, such as a large number of available materials containing a 18-F, 11-C, 13-N, or 15-O isotope. Such gamma ray-emitting materials can include any materials suitable for conveying information concerning physiologic parameters, including without limitation metabolic activity, tumor proliferative activity, oxygenation, and hypoxia, by way of example only. Any type of PET detector can be used as desired, including without limitation PET detectors having any number of crystals (not shown) sensitive to gamma ray emissions as just described. For example, the PET detectors 34, 35 can comprise one or more scintillation crystals comprising Sodium Iodide (NaI), Barium Fluoride (BaF2), Bi12SiO20 (BSO), Bi12GeO20 (BGO), Lu2SiO5:Ce (LSO), and the like.

However, the inventors have found that further advantages can be obtained by the use of flat panel PET detectors 34, 35. With reference to FIGS. 1 and 2, in some embodiments either or both of the PET detectors 34, 35 include a number of such crystals arranged in a substantially flat panel coupled to the respective arm(s) 30, 32. Such an arrangement of crystals can be used in conjunction with photomultiplier tubes (not shown) to detect photon emissions (e.g., gamma ray emissions) from one or more locations in or on the patient. Photomultiplier tubes and their manner of connection and operation in conjunction with scintillating crystals are well known to those in the art, and are not therefore described further herein.

The inventors have discovered that flat panel PET detectors 34, 35 can be used effectively to acquire functional images of a patient while occupying a relatively small amount of valuable space around the patient area 38. Also, when such detectors 34, 35 are mounted to move about the patient area 38 (such as by being mounted on arms 30, 32 of a gantry 18 as illustrated in FIGS. 1 and 2), improved functional images can be obtained. In other embodiments, either or both of the PET detectors 34, 35 need not necessarily be flat as just described, and can instead comprise a number of crystals arranged to define an arcuate detector surface facing the patient area 38 or a detector surface having any other shape desired. In such embodiments, the crystals can still be in sets coupled to the arms 30, 32 of the gantry 18 (e.g., a set of crystals coupled to each arm 30, 32) and movable about the patient area 38 by rotation of the gantry 18.

Each PET detector 34, 35 illustrated in FIGS. 1 and 2 has a substantially flat and planar face 42, 44. The faces 42, 44 of the PET detectors 34, 35 substantially face one another across the patient area 38, and can receive photons (e.g., gamma rays) emitted from the patient in diametrically opposite directions. Although the radiotherapy and imaging assembly 12 illustrated in FIGS. 1 and 2 has two PET detectors 34, 35, the radiotherapy and imaging assembly 12 can instead have any number of additional PET detectors 34, 35, such as one or more additional pairs of PET detectors 34, 35. Such additional PET detectors 34, 35 can be coupled to the gantry 18 by additional arms extending to locations adjacent the patient area 38.

By rotating the ring 22 illustrated in FIGS. 1 and 2, the arms 30, 32 also rotate, thereby rotating the PET detectors 34, 35 through respective ranges of positions about the patient area 38. Such adjustment enables a user to move the PET detectors 34, 35 in order to acquire images of the patient taken at different perspectives. The ring 22 can be rotatable through any range permitting such PET detector control. In some embodiments, the PET detectors 34, 35 can be rotated to any position about the patient area 38. For example, the ring 22 can rotate through a range of 360 or more degrees in order to move the PET detectors 34, 35 through the same range, although smaller ranges of motion are possible.

In the embodiment of FIGS. 1 and 2, the arm 24 of the radiotherapy accelerator 20, the arm 26 of the portal imager 28, and the arms 30, 32 of the PET detectors 34, 35 are illustrated at similar radial distances from the axis of rotation 36 of the ring 22. However, this relationship between the arms 24, 26, 30, 32 is not required. In some embodiments, the arms 24, 26 of the radiotherapy accelerator 20 and the portal imager 28 can extend from the ring 22 at different radial distances from the axis of rotation 36 of the ring 22. Also, in some embodiments either or both of these radial distances can be the same or different than the radial distance between the arms 30, 32 supporting the PET detectors 34, 35 and the axis of rotation 36. For example, the arms 30, 32 supporting the PET detectors 34, 35 can be located at a common radial distance that is smaller than the radial distances between the arms 24, 26 of the radiotherapy accelerator 20 and the portal imager 28. In such alternative embodiments, the ring 22 can be larger or smaller as needed to support the arms 24, 26, 30, 32.

It should also be noted that the radial distance between the axis of rotation 36 of the ring 22 and the arms 24, 26, 30, 32 can be different than the distances between the axis of rotation 36 and the radiotherapy accelerator 20, the portal imager 28, and the PET detectors 34, 35. In some embodiments, the radiotherapy accelerator 20 and the portal imager 28 are located at different radial distances from the axis of rotation 36. Also, in some embodiments either or both of these radial distances can be the same or different than the radial distances between the PET detectors 34, 35 and the axis of rotation 36. For example, the faces 42, 44 of the PET detectors 34, 35 can have a radial distance from the axis of rotation 36 that is smaller than the radial distances between the radiotherapy accelerator 20 and the portal imager 28.

The PET detectors 34, 35 illustrated in FIGS. 1 and 2 are located across the patient area 38 in circumferential positions spaced unequally between the radiotherapy accelerator 20 and the portal imager 28. Accordingly, the PET detectors 34, 35 are located adjacent the radiotherapy accelerator 20 and the portal imager 28, respectively. Such an arrangement of components can provide increased access to the patient at one or more circumferential positions about the patient area 38. In other embodiments, the PET detectors 34, 35 are substantially equally circumferentially spaced between the radiotherapy accelerator 20 and the portal imager 28.

As described above, the radiotherapy and imaging assembly 12 has a patient area 38 in which a patient is positioned for radiotherapy and imaging procedures. In some embodiments, the patient area 38 can be defined as all locations in which a patient can be positioned to receive radiation from the radiotherapy accelerator 20 and/or all locations in which an image can be retrieved from the PET imaging device 21. In some embodiments, for example, the patient area 38 includes a relatively thin disc-shaped volume defined by all locations about which the radiotherapy accelerator 20 is movable and in which the beam(s) from the radiotherapy accelerator 20 are received. In these and other embodiments, the patient area 38 also or instead includes a cylindrical area defined by all locations about which the PET imaging device 21 is movable and in which the PET imaging device 21 can retrieve an image.

Depending at least in part upon the size of the beam(s) emitted from the radiotherapy accelerator 20 and/or the size of the area detected by the PET detectors 34, 35, the patient area 38 can be larger or smaller. For example, in those embodiments in which the PET detectors 34, 35 are larger (and can retrieve images from a larger area between the PET detectors 34, 35), patient area 38 can have a longer cylindrical shape. As yet another example, the patient area 38 can be larger or smaller based upon the radial distances between the axis of rotation 36 and the radiotherapy accelerator 20, the portal imager 28, and the PET detectors 34, 35. Also, the patient area 38 in which radiotherapy can be administered and in which PET images can be obtained can be limited in those embodiments in which the radiotherapy accelerator 20, portal imager 28, and PET detectors 34, 35 are rotatable through ranges that are less than 360 degrees (e.g., in which rotation of the ring 22 is limited to less than 360 degrees).

With reference to FIG. 2, the various components of the radiotherapy and imaging assembly 12 can be coupled to a controller 50 for operation of the assembly 12. The controller 50 can be located on or in the housing 16 or can be located remote from the housing 16 as shown schematically in FIG. 2. If desired, information regarding system operation can be displayed or otherwise provided to the user by one or more displays, lights, sound-producing elements, and the like. In some embodiments, partial or full control of the radiotherapy and imaging assembly 12 can be enabled by controls 52 (e.g., monitor, touch screen display, keyboard, buttons, switches, dials, and the like) on the housing 16.

As shown in FIG. 1, some embodiments of the image-guided radiotherapy apparatus 10 comprise a patient support 14. The patient support 14 can be a table, a frame, or other structure suitable for supporting the patient as the radiotherapy accelerator 20, portal imager 28, PET detectors 34, 35, and other apparatus components are moved (as described above) during radiotherapy and imaging procedures. In some embodiments, the patient support 14 can be adjustable horizontally and vertically in order to move the patient with respect to the radiotherapy and imaging assembly 12. For example, the patient support 14 can have a top portion 54 movable horizontally with respect to a base 56, such as along one or more tracks 58, rails, slides, linear bearings, and the like. The top portion 54 can be movable manually or by one or more motors (not shown), actuators, or other prime movers. The base 56 can have an adjustable height controlled manually or by one or more motors (not shown), actuators, or other prime movers. Controls 59 can be coupled to the prime movers in order to vertically and horizontally adjust the patient support 14. Such patient supports and their manners of construction and operation are conventional in nature and are not therefore described further herein.

In some embodiments, other types of patient supports 14 can be used. By way of example only, the patient support 14 can be an adjustable or non-adjustable bed, stretcher, or other structure suitable for supporting the patient in any horizontal, inclined, declined, or tilted position. In other embodiments, the patient support can be a chair, wall, frame or other structure for supporting the patient in any orientation. Depending at least in part upon the type of patient support 14 used and the location and orientation of the radiotherapy and imaging assembly 12, the patient can be in a supine or prone position, on either side, in a seated or standing position, or in any other position. In this regard, the radiotherapy and imaging assembly 12 can be located and oriented in any manner suitable for receiving the patient in the patient area 38. For example, the radiotherapy and imaging assembly 12 can extend from an overhead position for a standing or seated patient. In still other embodiments, no patient support 14 is used.

In operation, a patient is positioned within the patient area 38 of the radiotherapy and imaging assembly 12. The ring 22 can be driven about the axis of rotation 36 to position the PET detectors 34, 35 in desired locations with respect to the patient area 38 (and the patient therein). Images can be acquired from the PET detectors 34, 35 in one or more of these locations. Using the information from such images, the ring 22 can be driven about the axis of rotation 36 to place the radiotherapy accelerator 20 at a desired position with respect to the patient area 38 (and patient therein), after which time the radiotherapy accelerator 20 can generate a beam of radiation at a desired location in or on the patient. In some embodiments, radiation treatment occurs after imaging by the PET detectors 34, 35, and in some cases can occur without moving the patient, without moving the PET detectors 34, 35 after imaging by the PET imaging device 21, and/or immediately after imaging by the PET imaging device 21. Accordingly, the location of the target (to which the beam of radiation from the radiotherapy accelerator 20 is to be directed) can be more accurately known, thereby reducing the degree of error in the administration of radiation to the patient. Also, the ability to more accurately target locations of the patient can enable a user to increase the dose of the radiation that is administered and/or reduce the dose administered to areas other than the target. In some embodiments, images can be acquired by the PET imaging device 21 while the radiotherapy accelerator 20 emits radiation to a target in or on the patient area 38. Also, in some embodiments, images can be acquired by the PET imaging device 21 after administration of therapeutic radiation for the purpose of detecting regions of physiologic change.

Figure 3:
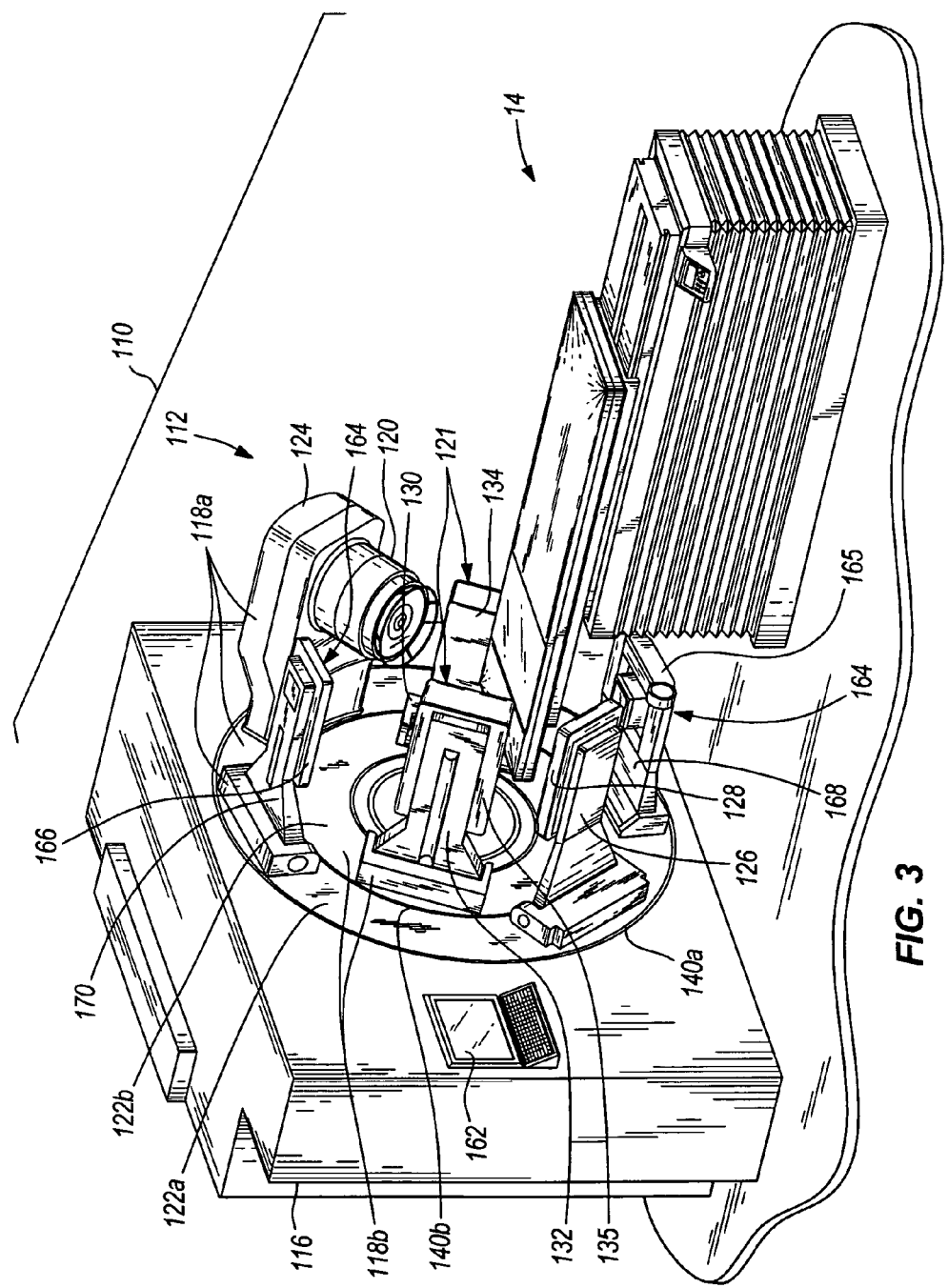
FIG. 3 is a perspective view of an image-guided radiotherapy apparatus according to a second embodiment of the present invention.
Figure 4:
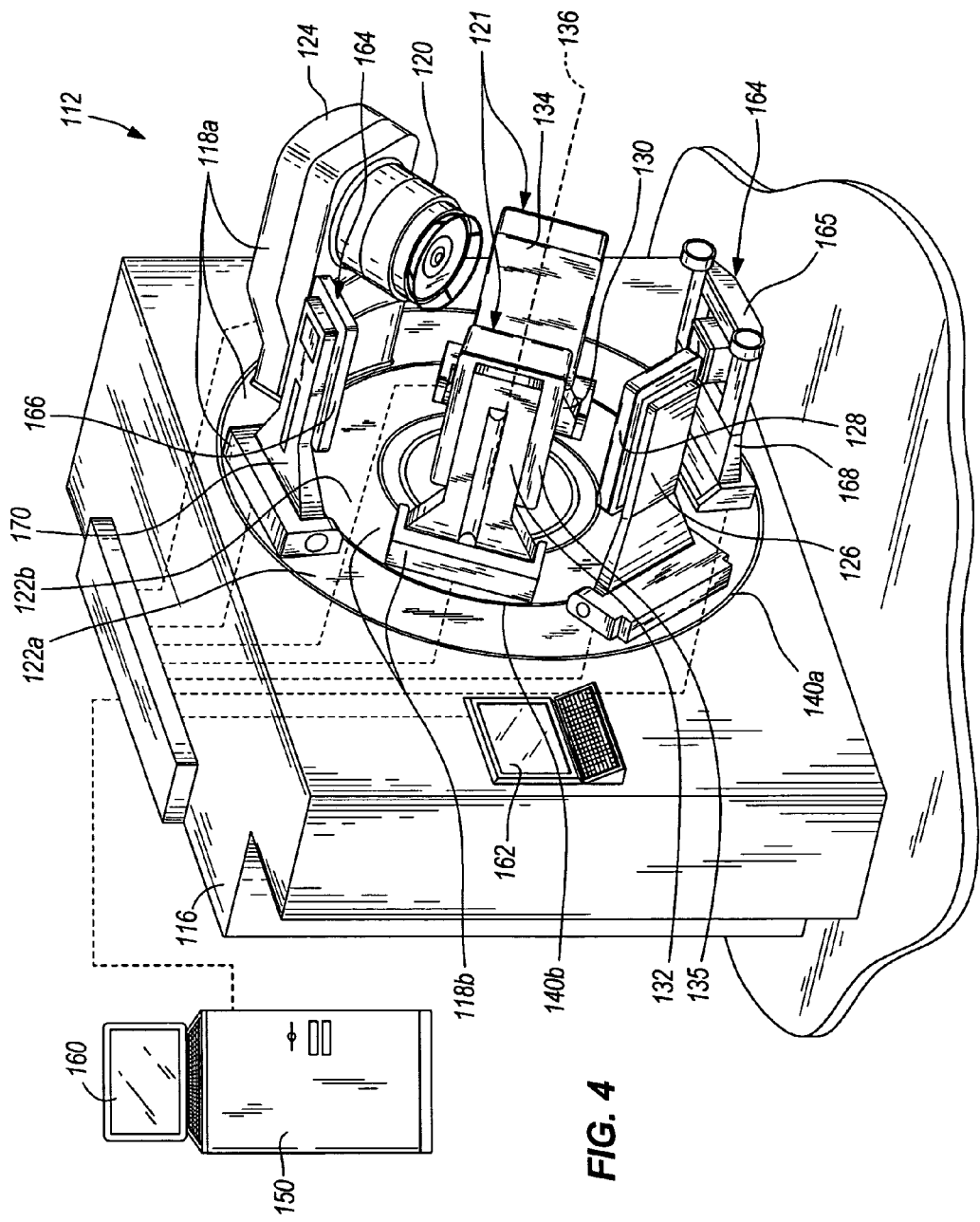
FIG. 4 is a perspective view of the radiotherapy and imaging assembly illustrated in FIG. 3.

FIGS. 3 and 4 illustrate another embodiment of an image-guided radiotherapy apparatus according to the present invention. The embodiment illustrated in FIGS. 3 and 4 employs much of the same structure and has many of the same operational features as the embodiments described above and illustrated in FIGS. 1 and 2. Accordingly, the following description focuses primarily upon those elements and features that are different from the embodiments described above. Reference should be made to the above description for additional information regarding the elements, features, and possible alternatives to the elements and features of the image-guided radiotherapy apparatus illustrated in FIGS. 3 and 4 and described below. Elements and features of the embodiment shown in FIGS. 3 and 4 that correspond to elements and features of the embodiment of FIGS. 1 and 2 are designated hereinafter in the 100 series of reference numbers.

The image-guided radiotherapy apparatus 110 illustrated in FIGS. 3 and 4 comprises a radiotherapy and imaging assembly 112 and a patient support 114. The radiotherapy and imaging assembly 112 illustrated in FIGS. 3 and 4 comprises a housing 116 and two gantries 118a, 118b movable with respect to the housing 116, a radiotherapy accelerator 120 coupled to a first gantry 118a, a CT imaging device 164 also coupled to the first gantry 118a, and a PET imaging device 121 coupled to the second gantry 1118b. As will now be described, the first gantry 118a is movable to different positions for purposes of administering radiotherapy and for CT image acquisition, and the second gantry 118b is movable to different positions for purposes of PET image acquisition.

The first gantry 118a in the illustrated embodiment of FIGS. 3 and 4 comprises a first ring 122a, a first arm 124 extending from the first ring 122 and to which the radiotherapy accelerator 120 is coupled, and a second arm 126 extending from the first ring 122a and to which a portal imager 128 is coupled. The second gantry 118b is similar to the first gantry 118a, and comprises a second ring 122b and third and fourth arms 130, 132 extending from the second ring 122b and to which PET detectors 134, 135 of the PET imaging device 121 are coupled. An X-ray emitter 165 and an X-ray detector 166 of the CT imaging device 164 are coupled to fifth and sixth arms 168, 170, respectively, extending from the first ring 122a. The first ring 122a is rotatable about an axis 136 to move the first, second, fifth, and sixth arms 124, 126, 168, 170 (and therefore the radiotherapy accelerator 120, portal imager 128, X-ray emitter 165 and X-ray detector 166) about the axis 136. The second ring 122b is rotatable about the axis 136 to move the third and fourth arms 130, 132 (and therefore and PET detectors 134, 135) about the axis 136.

Reference is hereby made to the description above regarding the gantry 18 in the embodiment of FIGS. 1 and 2 for further description of the first gantry 118a. In this regard, the first gantry 118a and first ring 122a illustrated in FIGS. 3 and 4 can be driven in any of the manners described above. Also, the first gantry 118a and/or the first and second arms 124, 126 can move along a first track 140a as described above with reference to the first and second arms 24, 26 and the track 40 in the embodiment of FIGS. 1 and 2.

The fifth and sixth arms 168, 170 can have any of the same features and be coupled to the first ring 122a and/or track 140a in any of the same manners and locations as the PET detector arms 30, 32 described above with reference to the embodiment of FIGS. 1 and 2. The CT imaging device 164 can be used to obtain anatomical images of a patient within the patient area 138, thereby providing additional information that can be useful in performing radiotherapy treatment with the radiotherapy accelerator 120 and the portal imager 128 (if employed).

By rotating the first ring 122a illustrated in FIGS. 3 and 4, the fifth and sixth arms 168, 170 also rotate, thereby rotating the X-ray emitter 165 and the X-ray detector 166 about the axis 136 through respective ranges of positions about the patient area 138. Such adjustment enables a user to move the X-ray emitter 165 and the X-ray detector 166 in order to acquire anatomical images of the patient taken at different perspectives. The first ring 122a can be rotatable through any range permitting such CT imaging device control. In some embodiments, the X-ray emitter 165 and the X-ray detector 166 can be rotated to any position about the patient area 138. For example, the first ring 122a can rotate through a range of 360 or more degrees in order to move the X-ray emitter 165 and the X-ray detector 166 through the same range, although smaller ranges of movement are possible.

The X-ray emitter 165 and the X-ray detector 166 illustrated in FIGS. 3 and 4 are located across the patient area 138 in circumferential positions spaced unequally between the radiotherapy accelerator 120 and the portal imager 128. Accordingly, the X-ray detector 166 and the X-ray emitter 165 are located adjacent the radiotherapy accelerator 120 and the portal imager 128, respectively. Such an arrangement of components can provide increased access to the patient at one or more circumferential positions about the patient area 138. In other embodiments, the X-ray emitter 165 and the X-ray detector 166 are substantially equally circumferentially spaced between the radiotherapy accelerator 120 and the portal imager 128.

With continued reference to FIGS. 3 and 4, the third and fourth arms 130, 132 (and therefore, the PET detectors 134, 135) are located on the second ring 122b rather than on the same ring as the radiotherapy accelerator 120 and the portal imager 128 as described with reference to the embodiment of FIGS. 1 and 2. The second ring 122b can have any of the features described above with reference to the first ring 122a, and can be received within a second track 140b similar to the first track 140a. The first and second tracks 140a, 140b can take any of the forms described above with reference to the track 40 in the first illustrated embodiment.

The first and second rings 122a, 122b illustrated in FIGS. 3 and 4 are substantially concentric, and can be driven independently of one another through at least a portion of their respective rotational ranges. For this purpose, the first and second rings 122a, 122b can be driven by respective prime movers (not shown) in any of the manners described above with reference to the embodiment illustrated in FIGS. 1 and 2. The first and second rings 122a, 122b need not necessarily be driven in the same manner, although such an arrangement can be employed if desired. For example, the first ring 122a can be driven by a ring gear and pinion assembly (such as a ring gear coupled to the first ring 122a and driven by one or more pinions drivably engaged with the ring gear) coupled to a prime mover, while the second ring 122b can be driven by another prime mover driving a shaft at the axis of rotation 136 (wherein the shaft is coupled by a frame, disc, hub, spokes, or other element(s) to the second ring 122b). Still other manners of independently driving the first and second rings 122a, 122b are possible, and fall within the spirit and scope of the present invention.

As an alternative to the use of the first ring 122a in the embodiment of FIGS. 3 and 4, any or all of the first, second, fifth, and sixth arms 124, 126, 168, 170 can be directly coupled to the first track 140a for movement therealong. Similarly, as an alternative to the use of the second ring 122b in the embodiment of FIGS. 3 and 4, either or both of the third and fourth arms 130, 132 can be directly coupled to the second track 140b for movement therealong. However, in those embodiments in which rings 122a, 122b are used as described above, it should be noted that corresponding tracks 140a, 140b are not required in all such embodiments.

By virtue of their locations on different rings 122a, 122b and substantially independent ring movement in at least a portion of the ranges of motion of the rings 122a, 122b, the PET imaging device 121 can be positioned to acquire images independently of the position of the radiotherapy accelerator 120. This capability can provide a user with significantly better information regarding the position of a target and the target's relationship to the beam trajectory of the radiotherapy accelerator 120, and can enable a user to adjust images generated by the PET imaging device 121 without changing the position of the radiotherapy accelerator 120.

In the illustrated embodiment of FIGS. 3 and 4, the CT imaging device 164 is located on the first ring 122a, and the PET imaging device 121 is located on the second ring 122b. However, in other embodiments both imaging devices 164, 121 can be located on the first ring 122a or the second ring 122b. Also, the radiotherapy accelerator 120 and portal imager 128 illustrated in FIGS. 3 and 4 are located on the first ring 122a. In other embodiments, the radiotherapy accelerator 120 and portal imager 128 can instead be located on the second ring 122b, either alone or with the PET imaging device 121 or the CT imaging device 164. In some embodiments, the CT imaging device 164 and PET imaging device 121 are located on the same ring 122 (and/or track 140) as the radiotherapy accelerator 120 and portal imager 128 (if used). In such embodiments, the image-guided radiotherapy apparatus 110 need not necessarily have two rings 122a, 122b (and/or tracks 140a, 140b), and can instead have one, three, or more rings 122 and/or tracks 140 as desired.

In still other embodiments, the radiation and imaging assembly 112 can have three concentric rings 122, each having the PET imaging device 121, the CT imaging device 164 and the radiotherapy accelerator 120 and portal imager 128, respectively. In some embodiments, the PET imaging device 121 can be located on the inner ring 122, and the CT imaging device 164 and radiotherapy accelerator 120 can be located on the middle and outer rings 122, respectively (or vice versa). In other embodiments, the CT imaging device 164 can be located on the inner ring 122, and the PET imaging device 121 and radiotherapy accelerator 120 can be located on the middle and outer rings 122, respectively (or vice versa). In still other embodiments, the radiotherapy accelerator 120 can be located on the inner ring 122, and the PET imaging device 121 and CT imaging device 164 can be located on the middle and outer rings 122, respectively (or vice versa). In those embodiments where the radiotherapy accelerator 120, PET imaging device 121, and CT imaging device 164 are each located on different rings 122, each ring 122 can be independently driven by a respective prime mover in any of the manners described above. In such embodiments, a user can be provided with greater ability to produce functional and anatomical images of the patient without disturbing the position of the radiotherapy accelerator 120.

In the embodiment of FIGS. 3 and 4, the arm 124 of the radiotherapy accelerator 120, the arm 126 of the portal imager 128, and the arms 168, 170 of the CT imaging device 164 are illustrated at similar radial distances from the axis of rotation 136 of the rings 122a, 122b. However, this relationship between the arms 124, 126, 168, 170 is not required. In some embodiments, the arms 124, 126 of the radiotherapy accelerator 120 and portal imager 128 can extend from the first ring 122a at different radial distances from the axis of rotation 136 of the rings 122a, 122b. Also, in some embodiments either or both of these radial distances can be the same or different than the radial distance between the arms 168, 170 of the CT imaging device 164 and the axis of rotation 136. For example, the arms 168, 170 of the CT imaging device 164 can be located at a common radial distance or at different radial distances that are smaller or larger than the radial distances between the arms 124, 126 of the radiotherapy accelerator 120 and the portal imager 128. In such alternative embodiments, the ring 122a can be larger or smaller as needed to support the arms 124, 126, 168, 170.

It should also be noted that the radial distance between the axis of rotation 136 of the rings 122a, 122b and the arms 124, 126, 168, 170 can be different than the distances between the axis of rotation 136 and the radiotherapy accelerator 120, the portal imager 128, the X-ray emitter 165, and the X-ray detector 166. In some embodiments, the radiotherapy accelerator 120 and the portal imager 128 are located at different radial distances from the axis of rotation 136. Also, in some embodiments the X-ray emitter 165 and the X-ray detector 166 are located at different radial distances from the axis of rotation 136.

In operation of the embodiment illustrated in FIGS. 3 and 4, a patient is positioned within the patient area 138 of the radiotherapy and imaging assembly 112. The first ring 122a can be driven about the axis of rotation 136 to position the X-ray emitter 165 and the X-ray detector 166 in desired locations with respect to the patient area 138 (and the patient therein). Also, the second ring 122b can be driven about the axis of rotation 136 to position the PET detectors 134, 135 in desired locations with respect to the patient area 138. Images can be acquired from the CT imaging device 164 and the PET imaging device 121 in one or more circumferential locations. In some embodiments, the anatomical CT image(s) can be combined with the PET functional image(s) to provide a combined image showing both types of information. Such combined images and the manners in which they can be generated are well known to those skilled in the art and are not therefore described further herein.

Using the information from the images of the PET imaging device 121 and/or the CT imaging device 164, the first ring 122a can be driven about the axis of rotation 136 to place the radiotherapy accelerator 120 at a desired position with respect to the patient area 138 (and patient therein), after which time the radiotherapy accelerator 120 can generate a beam of radiation at a desired location in or on the patient. Such movement of the first ring 122a and radiotherapy accelerator 120 can occur without changing the position of the PET detectors 134, 135, and in some embodiments can occur without interruption of the images generated by the PET detectors 134, 135. In some embodiments, radiation treatment occurs after imaging by the PET or CT imaging devices 121, 164, and in some cases can occur without moving the patient, without moving the PET or CT imaging devices 121, 164 after imaging by the PET or CT imaging devices 121, 164, and/or can occur immediately after imaging by the PET or CT imaging devices 121, 164.

In some embodiments, images can be acquired by the PET and/or CT imaging devices 121, 164 while the radiotherapy accelerator 120 emits radiation to a target in the patient area 138. In such embodiments, appropriate shielding can be positioned (if and when needed) to shield the PET detectors 134, 135 and/or the X-ray detector 166 from radiation emitted by the radiotherapy accelerator 120, thereby resulting in improved images generated by the PET and CT imaging devices 121, 164 in some cases. Also, in some embodiments, a user can monitor the target and the location of the beam (e.g., via a display 160, 162 coupled to the controller 150) during administration of the radiation. This ability can increase the accuracy and precision of the radiotherapy process.

Figure 5:
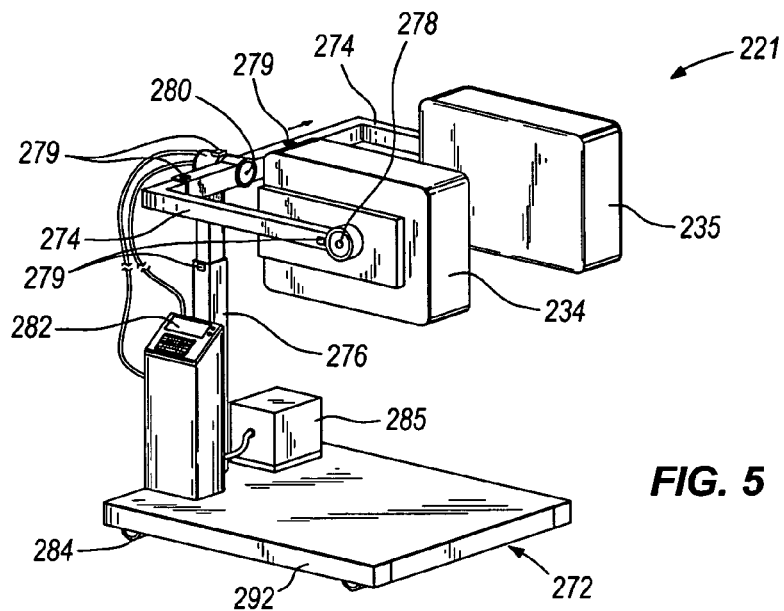
FIG. 5 is a perspective view of an imaging device according to a third embodiment of the present invention.
Figure 6:
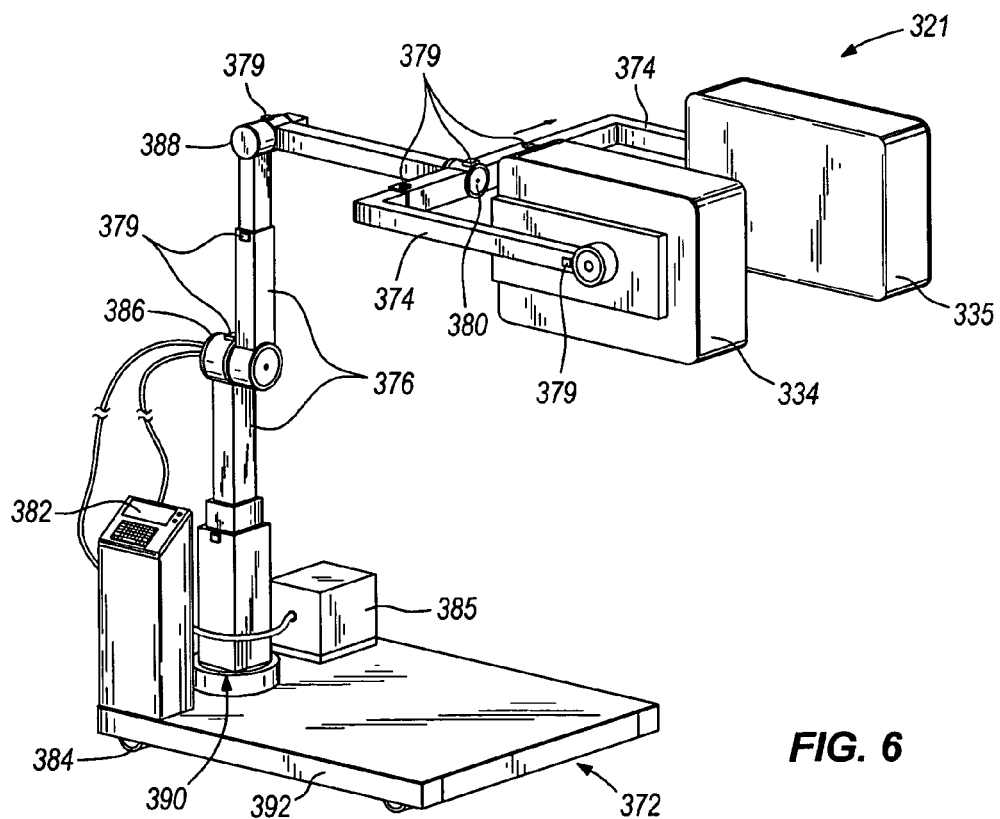
FIG. 6 is a perspective view of an imaging device according to a fourth embodiment of the present invention.
Figure 7:
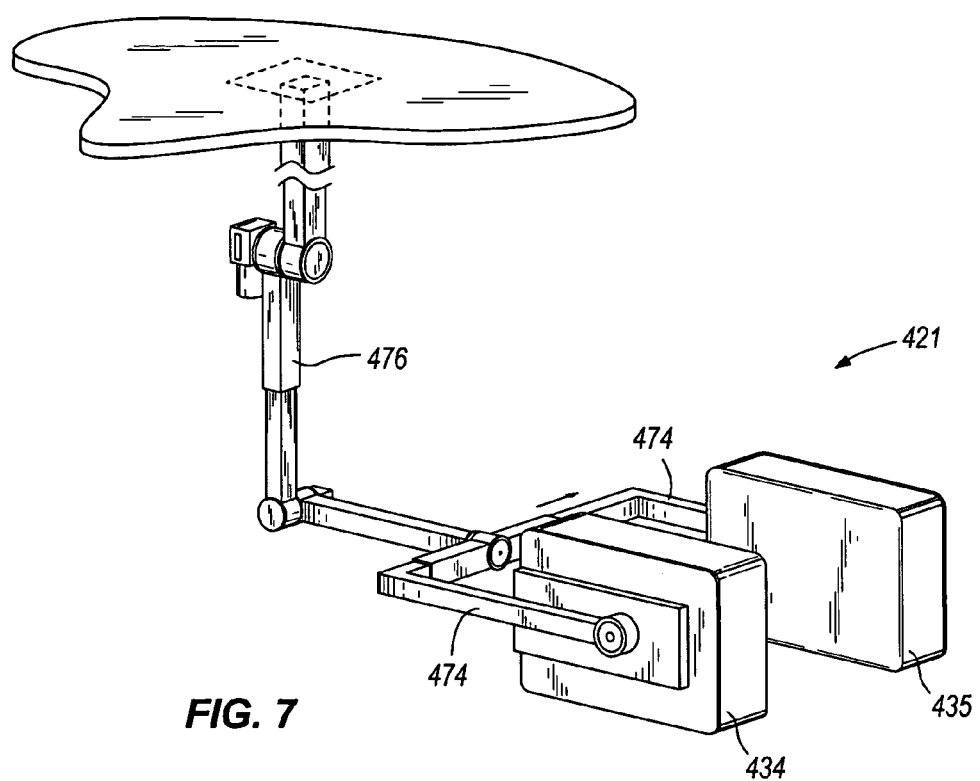
FIG. 7 is a perspective view of an imaging device according to a fifth embodiment of the present invention.

In the embodiments illustrated in FIGS. 1-4, the PET imaging device 21, 121 is coupled to a radiotherapy accelerator 20, 120 (and in some embodiments, a portal imager 28, 128), whether by a common gantry 118 or by concentric rings 122a, 122b and/or tracks 140a, 140b. However, in other embodiments the PET imaging device 21, 121 is not mechanically coupled to the radiotherapy accelerator 20, 120, and is instead a portable unit or is coupled to another structure. FIGS. 5-7 provide examples of such embodiments.

With reference first to FIG. 5, the PET imaging device 221 can have first and second PET detectors 234, 235 mounted to a portable frame 272. The PET detectors 234, 235 can be substantially the same as those described above with reference to the illustrated embodiments of FIGS. 1-4. Accordingly, reference is hereby made to the description above regarding the PET detectors 34, 134, 35, 135 of the first and second illustrated embodiments for more information regarding the features and operation of the PET detectors 234, 235 illustrated in FIG. 5.

The portable frame 272 of the PET imaging device 221 illustrated in FIG. 5 can have telescoping arms 274 enabling a user to adjust a distance between the PET detectors 234, 235 for different applications and/or can have a telescoping upright 276 for adjusting the height of the PET detectors 234, 235 with respect to a base 292. In addition or alternatively, the portable frame 272 can have rotatable joints 278 coupling the PET detectors 234, 235 to the arms 274 and/or can have a rotatable joint 280 coupling the arms 274 to the upright 276. Any of these features can be used alone or in combination to enable a user to position the PET imaging device 221 in a variety of different locations and orientations with respect to a patient area of a radiotherapy apparatus (not shown).

In many applications, it is desirable for a user to coordinate the position and orientation of the PET detectors 234, 235 with a radiotherapy accelerator of a radiotherapy apparatus (such as the radiotherapy accelerator 20, 120 illustrated in FIGS. 1-4). To this end, the PET imaging device 221 can be provided with a number of sensors detecting the position and orientation of the PET detectors 234, 235. By way of example only, the PET imaging device 221 illustrated in FIG. 5 can have sensors 279 mounted at the points of connection between the PET detectors 234, 235 and the telescoping arms 274, at the sliding joints of the telescoping arms 274, at the rotatable joint 280 coupling the telescoping arms 274 to the telescoping upright 276, and at the sliding joint of the telescoping upright 276. The sensors 279 can be coupled to a spatial coordinate location system 282 in any conventional manner, thereby automatically providing information regarding changes in position and orientation of the PET detectors 234, 235.

The spatial coordinate location system 282 can be used to set a reference location and orientation of the PET detectors 234, 235, and can provide this information (as well as any positional change information) to a controller (not shown) coupled to the radiotherapy apparatus. This information can be provided by a tethered connection to the controller or by a wireless connection between the spatial coordinate location system 282 and the controller. In the embodiment illustrated in FIG. 5, such information is transmitted wirelessly from the spatial coordinate location system 282. In order to prevent errors resulting from unintentional movement of the PET imaging device 221 after the reference location and orientation of the PET detectors 234, 235 has been set, the portable frame 272 can be provided with wheels or casters 284 that can be locked or retracted prior to use of the portable PET imaging device 221.

Power can be supplied to the portable PET imaging device 221 by a battery 285 or by a suitable power cord. Also, data from the PET detectors 234, 235 can be provided to a controller (not shown) coupled to the radiotherapy apparatus or to another location by a tethered or wireless connection. In the embodiment illustrated in FIG. 5, such information is transmitted wirelessly from the PET imaging device 221.

In some applications, greater portable frame adjustability is desirable. An example of a portable frame having such increased adjustability is illustrated in FIG. 6. The embodiment illustrated in FIG. 6 employs much of the same structure and has many of the same operational features as the embodiment described above and illustrated in FIG. 5. Accordingly, the following description focuses primarily upon those elements and features that are different from the FIG. 5 embodiment described above. Reference should be made to the above description for additional information regarding the elements, features, and possible alternatives to the elements and features of the PET imaging device 321 illustrated in FIG. 6 and described below. Elements and features of the embodiment shown in FIG. 6 that correspond to elements and features of the embodiment of FIG. 5 are designated hereinafter in the 300 series of reference numbers.

Like the PET imaging device 221 illustrated in FIG. 5, the PET imaging device 321 illustrated in FIG. 6 has first and second PET detectors 334, 335 rotatably coupled to respective telescoping arms 374, which in turn are rotatably coupled to a telescoping upright 376. However, the frame 372 of the portable PET imaging device 321 illustrated in FIG. 6 also has a rotatable joint 386 located between upper and lower portions of the upright 376, both of which are also provided with telescoping portions for height adjustability. Also, the portable frame 372 has two rotatable joints 380, 388 coupling the arms 374 to the telescoping upright 376, and a rotatable joint 390 coupling the upright 376 to a base 392 of the portable frame 372, thereby providing further adjustability of the PET detectors 334, 335. Like the portable frame 272 illustrated in FIG. 5, sensors can be located at the rotatable and telescoping joints of the portable frame 372 in order to monitor the position and orientation of the PET detectors 334, 335.

Another embodiment of a PET imaging device is illustrated in FIG. 7, and employs much of the same structure as the portable frame 372 illustrated in FIG. 6. Accordingly, elements and features of the embodiment shown in FIG. 7 that correspond to elements and features of the embodiment of FIG. 6 are designated hereinafter in the 400 series of reference numbers. Like the PET imaging device 321 illustrated in FIG. 6, the PET imaging device 421 illustrated in FIG. 7 has first and second PET detectors 434, 435 rotatably coupled to respective telescoping arms 474, which in turn are rotatably coupled to a telescoping upright 476. However, the PET imaging device 421 is mounted to a ceiling or other surface, and therefore has a fixed position with respect to a radiotherapy apparatus (not shown) and a patient area therein. The PET imaging device 421 can be used to easily move the PET detectors 434, 435 toward and away from the radiotherapy apparatus and associated patient area, and can instead be mounted to a wall, floor, or any other building structure for this purpose. For example, the PET imaging device 421 can be mounted in a location remote from the patient area, and can be drawn toward the patient area only as needed in preparation of or during a radiotherapy procedure.

Figure 8:
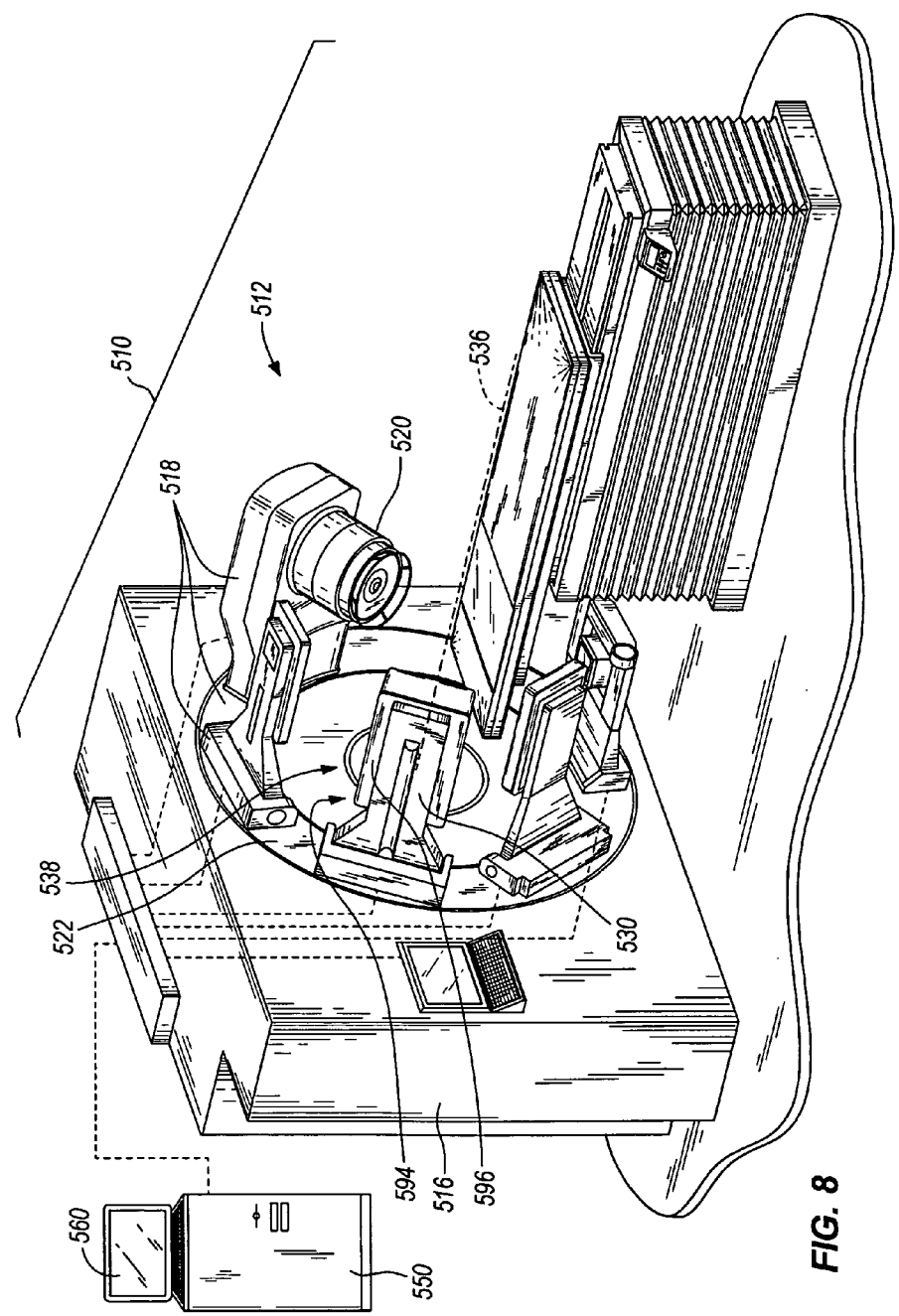
FIG. 8 is a perspective view of an image-guided radiotherapy apparatus according to a sixth embodiment of the present invention.

FIG. 8 illustrates another embodiment of an image-guided radiotherapy apparatus according to the present invention. The embodiment illustrated in FIG. 8 employs much of the same structure and has many of the same operational features as the embodiments described above with reference to FIGS. 1 and 2. Accordingly, the following description focuses primarily upon those elements and features that are different from the embodiments described above with reference to FIGS. 1 and 2. Reference should be made to the above description accompanying FIGS. 1 and 2 for additional information regarding the elements, features, and possible alternatives to the elements and features of the image-guided radiotherapy apparatus illustrated in FIG. 8 and described below. Elements and features of the embodiment shown in FIG. 8 that correspond to elements and features of the embodiment of FIGS. 1 and 2 are designated hereinafter in the 500 series of reference numbers.

The radiotherapy and imaging assembly 512 illustrated in FIG. 8 comprises a housing 516, a gantry 518 movable with respect to the housing 516, and a radiotherapy accelerator 520 coupled to the gantry 518. However, the radiotherapy and imaging assembly 512 has a Single Photon Emission Computer Tomography (SPECT) imaging device 594 rather than a PET imaging device. The SPECT imaging device 594 can comprise a SPECT detector 596 coupled to the gantry 518 and adapted to detect gamma rays emitted during decay of a gamma ray-emitting isotope. The gantry 518 is movable to different positions with respect to a patient area 538 for purposes of administering radiotherapy and for SPECT image acquisition.

The SPECT detector 596 can be coupled to an arm 530 of the gantry 518 and can be positioned in any of the manners described above with reference to the PET panels 34, 35 of the radiotherapy and imaging assembly 12 illustrated in FIGS. 1 and 2.

By rotating the ring 522 illustrated in FIG. 8, the arm 530 of the gantry 518 also rotates, thereby rotating the SPECT detector 596 through a range of positions about the patient area 538. Such adjustment enables a user to move the SPECT detector 596 in order to acquire images of the patient taken at different perspectives. The ring 522 can be rotatable through any range permitting such SPECT detector control. In some embodiments, the SPECT detector 596 can be rotated to any position about the patient area 538. For example, the ring 522 can rotate through a range of 360 or more degrees in order to move the SPECT detector 596 through the same range, although smaller ranges of movement are possible.

The radiotherapy and imaging assembly 512 illustrated in FIG. 8 has a single SPECT detector 596. In other embodiments, two or more SPECT detectors 596 located at different circumferential positions about the patient area 538 can be used to acquire images of the patient.

The radiotherapy and imaging assembly 512 illustrated in FIG. 8 is an example of how a SPECT detector 596 can be used in place of a PET detector in alternate embodiments of the present invention. In this regard, it will be appreciated that any or all of the PET detectors 34, 35, 134, 135, 234, 235, 334, 335, 434, 435 (and 634, 635 described below) in the embodiments herein can also be replaced by SPECT detectors 596 in still other embodiments of the present invention.

Figure 9:
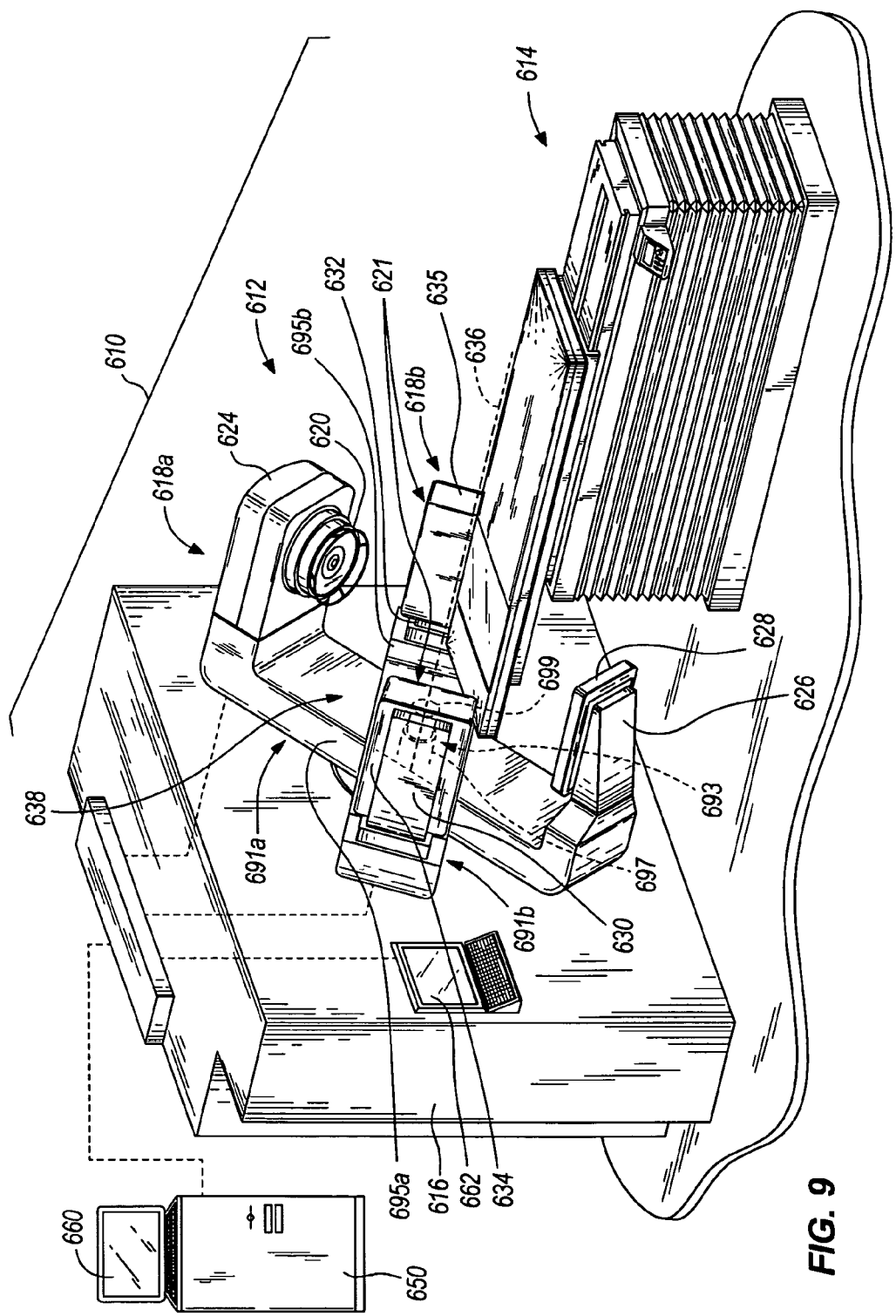
FIG. 9 is a perspective view of an image-guided radiotherapy apparatus according to a seventh embodiment of the present invention.

FIG. 9 illustrates another embodiment of an image-guided radiotherapy apparatus according to the present invention. The embodiment illustrated in FIG. 9 employs much of the same structure and has many of the same operational features as the embodiments described above and illustrated in FIGS. 1 and 2. Accordingly, the following description focuses primarily upon those elements and features that are different from the embodiments described above. Reference should be made to the above description for additional information regarding the elements, features, and possible alternatives to the elements and features of the image-guided radiotherapy apparatus illustrated in FIG. 9 and described below. Elements and features of the embodiment shown in FIG. 9 that correspond to elements and features of the embodiment of FIGS. 1 and 2 are designated hereinafter in the 600 series of reference numbers.

The image-guided radiotherapy apparatus 610 illustrated in FIG. 9 comprises a radiotherapy and imaging assembly 612 and a patient support 614. The radiotherapy and imaging assembly 612 illustrated in FIG. 9 comprises a housing 616 and two gantries 618a, 618b movable with respect to the housing 616, a radiotherapy accelerator 620 coupled to a first gantry 618a, and a PET imaging device 621 coupled to the second gantry 618b. As will now be described, the first gantry 618a is movable to different positions for purposes of administering radiotherapy, and the second gantry 618b is movable to different positions for purposes of PET image acquisition.

The first and second gantries 618a, 618b in the illustrated embodiment of FIG. 9 each comprise a frame 691a, 691b coupled to and extending from an axle 693. The axle 693 can be driven in any conventional manner, such as by a prime mover (not shown) directly or indirectly coupled to the axle 693. Accordingly, by rotating the axle 693, the frames 691a, 691b are rotated.

The frames 691a, 691b can each comprise any number and type of elements radially extending from the axle 693.

In the illustrated embodiment of FIG. 9, for example, each frame 691a, 691b includes a beam 695a, 695b extending radially from opposite sides of the axle 693. In other embodiments, each frame 691a, 691b can comprise any number of plates, rods, and other elements coupled in any manner and extending radially from the axle 693.

With continued reference to FIG. 9, the first gantry 618a further comprises a first arm 624 extending from the first beam 695a and to which the radiotherapy accelerator 620 is coupled, and a second arm 626 extending from the first beam 695a and to which the portal imager 628 is coupled. The second gantry 618b further comprises third and fourth arms 630, 632 extending from the second beam 695b and to which PET detectors 634, 635 of the PET imaging device 621 are coupled. The first beam 695a is rotatable about an axis 636 to move the first and second arms 624, 626 (and therefore the radiotherapy accelerator 620 and portal imager 628) about the axis 636. The second beam 695b is rotatable about the axis 636 to move the third and fourth arms 630, 632 (and therefore and PET detectors 634, 635) about the axis 636.

In those embodiments in which a portal imager 628 is employed, the portal imager 628 can be rotatably coupled to the second arm 626 and/or the second arm 626 can be rotatably coupled to the first beam 695a, thereby enabling the portal imager 628 to be moved with respect to the patient area 638. This ability to move the portal imager 628 can, in some embodiments, enable a user to rotate the portal imager 628 in order to provide greater access to the patient area 638 and/or to reduce the number of items extending in a direction away from the housing 616.

By rotating the first beam 695a illustrated in FIG. 9, the first and second arms 624, 626 also rotate, thereby rotating the radiotherapy accelerator 620 and portal imager 628 about the axis 636 through respective ranges of positions about the patient area 638. Such adjustment enables a user to move the radiotherapy accelerator 620 to change the trajectory of a beam of radiation exiting from the radiotherapy accelerator 620, and enables the user to change the position of the portal imager 628 in order to acquire different images of the patient therefrom. The first beam 695a can be rotatable through any range permitting such beam and portal imager control. In some embodiments, the radiotherapy accelerator 620 is rotatable to any position about the patient area 638. For example, the first beam 695a can rotate through a range of 360 or more degrees in order to move the radiotherapy accelerator 620 through the same range, although smaller ranges of movement are possible.

By rotating the second beam 695b illustrated in FIG. 9, the third and fourth arms 630, 632 also rotate, thereby rotating the PET detectors 634, 635 about the axis 636 through respective ranges of positions about the patient area 638. Such adjustment enables a user to move the PET detectors 634, 635 in order to acquire images of the patient taken at different perspectives. The second beam 695b can be rotatable through any range permitting such PET detector control. In some embodiments, the PET detectors 634, 635 can be rotated to any position about the patient area 638. For example, the second beam 695b can rotate through a range of 360 or more degrees in order to move the PET detectors 634, 635 through the same range, although smaller ranges of motion are possible.

In some embodiments, the first and second beams 695a, 695b are fixed with respect to one another, in which case both beams 695a, 695b rotate together upon rotation of the axle 693 to which the beams 695a, 695b are coupled. In other embodiments, the beams 695a, 695b are rotatable about the axis of rotation 636 through a range of positions with respect to one another. Such rotation is possible, for example, by drivably coupling each beam 695a, 695b to a different portion of the axle 693. In the illustrated embodiment of FIG. 9, the axle 693 has a first portion 697 and a second portion 699 located within a hollow center of the first portion 697 and extending beyond an end of the first portion 697. Both portions 697, 699 can be drivably connected to respective prime movers in any conventional manner. Also, the first beam 695a can be drivably connected to the first portion 697 of the axle 693 in any conventional manner, and the second beam 695b can be drivably connected to the second portion 699 of the axle 693 in any conventional manner (or vice versa). In this way, the first portion 697 of the axle 693 and the first beam 695a thereon can be rotated through a range of positions independently of the second portion 699 of the axle 693 and the second beam 695b thereon. The first portion 697 of the axle 693 (and therefore the first beam 695a and the radiotherapy accelerator 620 and portal imager 628) can be rotatable through any range with respect to the second portion 699 of the axle 693 (and therefore, the second beam 695b and the PET detectors 634, 635). For example, in some embodiments the first portion 697 of the axle 693 can be rotatable through a range of 360 degrees or more with respect to the second portion 699 of the axle 693, although smaller ranges of independent motion are possible.

With continued reference to the embodiment illustrated in FIG. 9, the first beam 695a extends to longer radial positions than the second beam 695b, enabling the radiotherapy accelerator 620 and the portal imager 628 to rotate about the patient area 638 without interference with the PET detectors 634, 635. In other embodiments, however, the first and second beams 695a, 695b can be dimensioned so that the radiotherapy accelerator 620 and/or the portal imager 628 will interfere with either or both PET detectors 634, 635 upon sufficient rotation of the first beam 695a with respect to the second beam 695b, in which case the first beam 695a (and the radiotherapy accelerator 620 and portal imager 628) can be movable through a limited amount of rotation with respect to the second beam 695b (and the PET detectors 634, 635).

In the embodiment illustrated in FIG. 9, the second beam 695b and the third and fourth arms 630, 632 supporting the PET detectors 634, 635 are nested within the first beam 695a and the first and second arms 624, 626 supporting the radiotherapy accelerator 620 and portal imager 628, thereby enabling rotation of the first beam 695a with respect to the second beam 695b as described above. In other embodiments, the radiotherapy accelerator 620 and portal imager 628 can instead be supported by the second beam 695b, and the PET detectors 634, 635 can be supported by the first beam 695a.

The image-guided radiotherapy apparatus 610 can have any number of gantries 618, any of which can be rotatable with respect to one or more of the other gantries 618. For example, the image-guided radiotherapy apparatus 610 can have three or more gantries 618 supporting different imaging and radiotherapy devices, such as two or more nested gantries 618 supporting any number of PET detectors 634, 635. As another example, the image-guided radiotherapy apparatus 610 can have a single gantry 618 to which the radiotherapy accelerator 620 and the PET detectors 634, 635 are coupled. In some embodiments, the image-guided radiotherapy apparatus 610 includes a CT imaging device (e.g., an X-ray emitter and an X-ray detector) (not shown) supported by a separate gantry or coupled to a gantry 618a, 618b that also supports the PET imaging device 621 and/or the radiotherapy accelerator 620. In such embodiments, two or more gantries 618 can be nested (as described above) in any arrangement to enable relative rotational movement between the gantries 618. Alternatively, a single gantry 618 can support the PET imaging device 621 and the CT imaging device on the same or different gantry 618 as the radiotherapy accelerator 620.

By virtue of their locations on different beams 695*a*, 695*b* and substantially independent beam movement in at least a portion of the ranges of motion of the beams 695*a*, 695*b*, the PET imaging device 621 illustrated in FIG. 9 can be positioned to acquire images independently of the position of the radiotherapy accelerator 620. This capability can provide a user with significantly better information regarding the position of a target and the target's relationship to the beam trajectory of the radiotherapy accelerator 620, and can enable a user to adjust images generated by the PET imaging device 621 without changing the position of the radiotherapy accelerator 620.

In the embodiment illustrated in FIG. 9, each gantry 618*a*, 618*b* has a rotatable beam 695*a*, 695*b* for supporting radiotherapy and imaging components of the image-guided radiotherapy apparatus 610. However, in other embodiments the image-guided radiotherapy apparatus 610 can have any combination of gantry types described herein, such as an image-guided radiotherapy apparatus 610 having one or more beam-type gantries 618 and one or more ring-type gantries as described above with respect to the embodiments of FIGS. 1-4, an image-guided radiotherapy apparatus 610 having one or more beam-type gantries 618 and one or more arms movable along track(s) as also described above with respect to the embodiments of FIGS. 1-4, and the like. Any combination of gantry types can be utilized in different embodiments of the present invention.

In operation of the embodiment illustrated in FIG. 9, a patient is positioned within the patient area 638 of the radiotherapy and imaging assembly 612. The second beam 695*b* can be driven about the axis of rotation 636 to position the PET detectors 634, 635 in desired locations with respect to the patient area 638. Images can be acquired from the PET imaging device 621 in one or more circumferential locations. Using the information from the images of the PET imaging device 621, the first beam 695*a* can be driven about the axis of rotation 636 to place the radiotherapy accelerator 620 at a desired position with respect to the patient area 638 (and patient therein), after which time the radiotherapy accelerator 620 can generate a beam of radiation at a desired location in or on the patient. Such movement of the first beam 695*a* and radiotherapy accelerator 620 can occur without changing the position of the PET detectors 634, 635, and in some embodiments can occur without interruption of the images generated by the PET detectors 634, 635. In some embodiments, radiation treatment occurs after imaging by the PET imaging device 621, and in some cases can occur without moving the patient, without moving the PET imaging device 621 after imaging by the PET imaging device 621, and/or can occur immediately after imaging by the PET imaging device 621.

In some embodiments, images can be acquired by the PET imaging device 621 while the radiotherapy accelerator 620 emits radiation to a target in the patient area 638. In such embodiments, a user can monitor the target and the location of the beam (e.g., via a display 660, 662 coupled to a controller 650) during administration of the radiation. This ability can increase the accuracy and precision of the radiotherapy process.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention as set forth in the appended claims.

For example, the image-guided radiotherapy apparatus 10, 110, 510, 610 and the radiotherapy and imaging assembly 12, 112, 212, 312, 412, 512, 612 according to the various embodiments described herein can be used to treat a patient and acquire images of any part of a patient, and can be shaped and dimensioned as suitable for any part of a patient. Also, reference is made herein to images of a patient and to a patient positioned within a patient area 38, 138, 538, 638. As used herein and in the appended claims, such references regard any part or all of a patient.

As described above, the PET (and SPECT) imaging devices 21, 121, 221, 321, 421, 594, 621 can be used in conjunction with a radiotherapy accelerator 20, 120, 520, 620 to provide images of a patient within a patient area 38, 138, 538, 638. As also described above, the patient area 38, 138, 538, 638 can be defined by an area within which a patient can be positioned to receive radiation from the radiotherapy accelerator 20, 120, 520, 620 and/or all locations in which an image can be retrieved by the PET (or SPECT) imaging device 21, 121, 221, 321, 421, 594, 621. However, the PET and SPECT imaging devices 21, 121, 221, 321, 421, 594, 621 can be used in a number of other applications in which a medical procedure is performed on a patient. In such cases, the PET and SPECT imaging devices 21, 121, 221, 321, 421, 594, 621 can define or partially define a patient area in which images of the patient are to be taken and in which the medical procedure is to be performed. Examples of such other applications include without limitation any type of manual, automated, or semi-automated surgical procedure, biopsies, testing, and the like.

What is claimed is:

1. An image-guided radiotherapy apparatus, comprising:
   a gantry movable about a patient area;
   a radiation source from which therapeutically effective radiation is emitted toward the patient area, the radiation source coupled to and movable with the gantry to different positions about the patient area; and
   a gamma ray photon imaging device comprising a gamma ray photon detector proximate the patient area and positioned to receive and detect gamma ray photons emitted from within the patient area, the gamma ray photon detector movable to different positions about the patient area to obtain different images of a patient within the patient area.

2. The apparatus as claimed in claim 1, wherein the gantry is a first gantry, the apparatus further comprising a second gantry coupled to the first gantry, wherein the gamma ray photon detector is coupled to and movable with the second gantry to different positions about the patient area.

3. The apparatus as claimed in claim 1, wherein:
   the gantry comprises an arm extending to a location adjacent the patient area; and
   the radiation source is located on the arm.

4. The apparatus as claimed in claim 3, wherein the arm is rotatable about an axis passing through the patient area.

5. The apparatus as claimed in claim 1, wherein the gantry is a first gantry, the apparatus further comprising a second gantry having an arm extending to a location adjacent the patient area, wherein the gamma ray photon detector is located on the arm.

6. The apparatus as claimed in claim 5, wherein:
the arm is a first arm;
the location is a first location; and
the first gantry has a second arm extending to a second location adjacent the patient area, wherein the radiation source is located on the second arm.

7. The apparatus as claimed in claim 6, wherein the first and second arms are rotatable about an axis passing through the patient area.

8. The apparatus as claimed in claim 6, wherein the gamma ray photon imaging device is a SPECT imaging device.

9. The apparatus as claimed in claim 6, wherein the gamma ray photon imaging device is a PET imaging device.

10. The apparatus as claimed in claim 9, wherein the gamma ray photon detector has a substantially planar surface adapted to receive and detect gamma ray photons from the patient area.

11. The apparatus as claimed in claim 9, wherein:
the gamma ray photon detector is a first gamma ray photon detector;
the gamma ray photon imaging device further comprises a second gamma ray photon detector; and
at least a portion of the first and second gamma ray photon detectors face one another.

12. The apparatus as claimed in claim 11, wherein the first and second gamma ray photon detectors substantially face one another across the patient area.

13. The apparatus as claimed in claim 11, wherein the first and second gamma ray photon detectors each have a substantially planar surface adapted to receive and detect gamma ray photons from the patient area.

14. The apparatus as claimed in claim 1, wherein the gantry is rotatable about the patient area.

15. The apparatus as claimed in claim 14, wherein the gantry is a first gantry, the apparatus further comprising a second gantry movable about the patient area, wherein the gamma ray photon detector is coupled to and movable with the second gantry to different positions about the patient area.

16. The apparatus as claimed in claim 15, wherein the second gantry is rotatable about the patient area.

17. The apparatus as claimed in claim 16, wherein the gamma ray photon imaging device is a SPECT imaging device.

18. The apparatus as claimed in claim 16, wherein the gamma ray photon imaging device is a PET imaging device.

19. The apparatus as claimed in claim 18, wherein the gamma ray photon detector has a substantially planar surface adapted to receive and detect gamma ray photons from the patient area.

20. The apparatus as claimed in claim 18, wherein:
the gamma ray photon detector is a first gamma ray photon detector;
the gamma ray photon imaging device further comprises a second gamma ray photon detector; and
at least a portion of the first and second gamma ray photon detectors face one another.

21. The apparatus as claimed in claim 20, wherein the first and second gamma ray photon detectors substantially face one another across the patient area.

22. The apparatus as claimed in claim 20, wherein the first and second gamma ray photon detectors each have a substantially planar surface adapted to receive and detect gamma ray photons from the patient area.

23. The apparatus as claimed in claim 15, wherein the first gantry is rotatable through a range of motion about the patient area substantially independently of movement of the second gantry.

24. The apparatus as claimed in claim 1, wherein the radiation source comprises a linear accelerator.

25. The apparatus as claimed in claim 1, wherein the gamma ray photon imaging device is a PET imaging device.

26. The apparatus as claimed in claim 25, wherein the gamma ray photon detector has a substantially planar surface adapted to receive and detect gamma ray photons from the patient area.

27. The apparatus as claimed in claim 25, wherein:
the gamma ray photon detector is a first gamma ray photon detector;
the gamma ray photon imaging device further comprises a second gamma ray photon detector; and
at least a portion of the first and second gamma ray photon detectors face one another.

28. The apparatus as claimed in claim 27, wherein the first and second gamma ray photon detectors substantially face one another across the patient area.

29. The apparatus as claimed in claim 27, wherein the first and second gamma ray photon detectors each have a substantially planar surface adapted to receive and detect gamma ray photons from the patient area.

30. The apparatus as claimed in claim 25, further comprising a portable frame to which the gamma ray photon detector is mounted, wherein the portable frame is movable to and from positions adjacent the patient area.

31. The apparatus as claimed in claim 25, wherein the gamma ray photon detector is coupled to the gantry.

32. The apparatus as claimed in claim 31, wherein:
the gantry is a first gantry; and
the gamma ray photon detector is coupled to the first gantry via a second gantry; and
the gamma ray photon detector is movable with the second gantry to different positions about the patient area.

33. The apparatus as claimed in claim 1, wherein the gamma ray photon imaging device is a SPECT imaging device.

34. The apparatus as claimed in claim 1, further comprising a portable frame to which the gamma ray photon detector is mounted, wherein the portable frame is movable to and from positions adjacent the patient area.

35. An image-guided radiotherapy apparatus for treatment of a patient, comprising:
a gantry;
a radiotherapy accelerator adapted to generate a therapeutically effective beam of at least one of X-rays, gamma rays, and electrons, the radiotherapy accelerator coupled to the gantry and movable through a range of different positions and orientations to change trajectory of the therapeutically effective beam; and
a PET detector coupled to the gantry and movable through a range of different positions and orientations about a patient area in which a patient's PET image can be taken, the patient area comprising at least one location through which the therapeutically effective beam of the radiotherapy accelerator passes in at least one position and orientation of the radiotherapy accelerator.

36. The apparatus as claimed in claim 35, wherein:
the gantry is a first gantry;
the PET detector is coupled to the first gantry via a second gantry; and
the second gantry is movable through a range of positions to move the PET detector.

37. The apparatus as claimed in claim 36, wherein:
the first and second gantries are movable through respective ranges of motion; and
the first and second gantries are movable substantially independently with respect to one another in at least a portion of their respective ranges of motion.

38. The apparatus as claimed in claim 35, wherein:
the gantry is a first gantry;
the radiotherapy accelerator is coupled to the first gantry via a second gantry; and
the second gantry is movable through a range of positions to move the radiotherapy accelerator.

39. The apparatus as claimed in claim 35, wherein:
the gantry has first and second arms extending in spaced relationship with respect to one another; and
the PET detector is located on the first arm adjacent the patient area in at least one position of the PET detector.

40. The apparatus as claimed in claim 39, wherein the PET detector is a first PET detector, the apparatus further comprising a second PET detector located on the second arm adjacent the patient area in at least one position of the second PET detector.

41. The apparatus as claimed in claim 35, wherein:
the PET detector has a face adapted to detect gamma ray photons; and
the face is substantially planar.

42. The apparatus as claimed in claim 41, wherein the PET detector is a first PET detector, the apparatus further comprising a second PET detector movable through a range of different positions and orientations with respect to the patient area, wherein at least part of the patient area is located between the first and second PET detectors.

43. The apparatus as claimed in claim 35, wherein the PET detector is a first PET detector, the apparatus further comprising a second PET detector movable through a range of different positions and orientations with respect to the patient area, wherein at least part of the patient area is located between the first and second PET detectors.

44. A method of administering image-guided radiotherapy, comprising:
adjusting at least one of a position and orientation of a radiotherapy radiation source with respect to a patient;
changing a radiation trajectory of the radiotherapy radiation source to a desired radiation trajectory by adjusting the at least one of a position and orientation of the radiotherapy radiation source, the desired radiation trajectory passing through the patient;
emitting a beam of therapeutically effective radiation from the radiotherapy radiation source along the desired radiation trajectory;
adjusting at least one of a position and orientation of a gamma ray photon imaging device with respect to the patient;
detecting gamma ray photons with the gamma ray photon imaging device, the gamma ray photons emitted from the patient proximate a location along the desired radiation trajectory at which the desired radiation trajectory intersects the patient; and
generating an image representative of the patient based at least in part upon locations on the gamma ray photon imaging device at which gamma ray photons are detected.

45. The method as claimed in claim 44, wherein the beam of therapeutically effective radiation comprises at least one of X-rays, gamma rays, and electrons.

46. The method as claimed in claim 45, wherein detecting gamma ray photons occurs at least partially while emitting the beam.

47. The method as claimed in claim 44, wherein adjusting at least one of the position and orientation of the radiotherapy radiation source further comprises rotating the radiotherapy radiation source about an axis.

48. The method as claimed in claim 47, wherein adjusting at least one of the position and orientation of the radiotherapy radiation source occurs substantially independently of adjusting at least one of the position and orientation of the gamma ray photon imaging device.

49. The method as claimed in claim 44, wherein adjusting at least one of the position and orientation of the gamma ray photon imaging device further comprises rotating the gamma ray photon imaging device about an axis.

50. The method as claimed in claim 49, wherein adjusting at least one of the position and orientation of the gamma ray photon imaging device further comprises rotating first and second gamma ray photon detectors about an axis, wherein the first and second gamma ray photon detectors are located on opposite sides of the location at which the desired radiation trajectory intersects the patient.

51. The method as claimed in claim 50, wherein:
the first and second gamma ray photon detectors each have a face adapted to detect gamma ray photons; and
the face of each of the first and second gamma ray photon detectors is substantially planar.

52. The method as claimed in claim 49, wherein:
the axis is a first axis; and
adjusting at least one of the position and orientation of the radiotherapy radiation source further comprises rotating the radiotherapy radiation source about a second axis.

53. The method as claimed in claim 52, wherein the first and second axes are collinear.

54. The method as claimed in claim 52, wherein adjusting at least one of the position and orientation of the radiotherapy radiation source occurs substantially independently of adjusting at least one of the position and orientation of the gamma ray photon imaging device.

55. The method as claimed in claim 44, wherein detecting gamma ray photons comprises detecting gamma ray photons substantially simultaneously on opposite sides of a patient.

56. The method as claimed in claim 44, wherein the gamma ray photon imaging device is a PET imaging device.

57. The method as claimed in claim 56, wherein detecting gamma ray photons comprises detecting gamma ray photons on a flat detector face of the PET imaging device.

58. The method as claimed in claim 44, wherein the gamma ray photon imaging device is a SPECT imaging device.

59. The method as claimed in claim 44, wherein:
the gamma ray photon imaging device comprises at least one gamma ray photon detector coupled to a portable frame; and
adjusting at least one of the position and orientation of the gamma ray photon imaging device comprises moving the portable frame toward the radiotherapy radiation source.

* * * * *